United States Patent [19]

Archibald

[11] Patent Number: 4,705,506
[45] Date of Patent: Nov. 10, 1987

[54] MULTIPLE SOLUTION IV SYSTEM WITH SETUP ERROR PROTECTION

[75] Inventor: G. Kent Archibald, White Bear Lake, Minn.

[73] Assignee: Minnesota Mining and Manufacturing Company, St. Paul, Minn.

[21] Appl. No.: 798,228

[22] Filed: Nov. 14, 1985

Related U.S. Application Data

[63] Continuation-in-part of Ser. No. 676,009, Nov. 29, 1984.

[51] Int. Cl.$^4$ .............................................. A61M 5/14
[52] U.S. Cl. ........................................ 604/81; 604/67;
604/250; 604/246; 128/DIG. 13; 364/173;
364/413
[58] Field of Search ..................... 604/51–53,
604/65–67, 80, 81, 131, 151, 153, 245, 246,
248–250; 128/DIG. 12, DIG. 13; 137/636.1,
595, 553; 251/4–10, 67, 68, 74; 222/130, 136,
137, 145, 144.5; 364/413, 415, 172, 173, 510

[56] References Cited

U.S. PATENT DOCUMENTS

| | | |
|---|---|---|
| Re. 16,251 | 1/1926 | Schellberg . |
| 1,683,723 | 9/1928 | Myres . |
| 2,112,160 | 3/1938 | Johnson ............................... 128/234 |
| 2,591,216 | 4/1952 | Thompson et al. ................. 137/139 |
| 2,594,639 | 4/1952 | Gossett .................................. 285/210 |
| 2,710,004 | 6/1955 | Stamper ................................ 128/214 |
| 2,866,457 | 12/1958 | Moore .................................. 128/214 |
| 2,999,499 | 9/1961 | Willet .................................... 128/214 |
| 3,016,915 | 1/1962 | Moeller, Jr. .......................... 137/595 |
| 3,575,161 | 4/1971 | London ................................. 128/2.05 |
| 3,895,649 | 7/1975 | Ellis ....................................... 137/595 |
| 4,094,318 | 6/1978 | Burke et al. ..................... 128/214 E |
| 4,114,617 | 9/1978 | Turner et al. ..................... 128/214 R |
| 4,217,993 | 8/1980 | Jess et al. ..................... 128/DIG. 13 |
| 4,230,151 | 10/1980 | Jonsson ................................. 137/595 |
| 4,236,880 | 12/1980 | Archibald ............................ 417/478 |
| 4,265,240 | 5/1981 | Jenkins . |
| 4,316,460 | 2/1982 | Genese ............................. 128/214 R |
| 4,324,238 | 4/1982 | Genese ............................. 128/214 G |
| 4,391,598 | 7/1983 | Thompson ........................... 604/65 |
| 4,397,642 | 8/1983 | Lamadrid ............................. 604/245 |
| 4,425,116 | 1/1984 | Bilstad et al. ......................... 604/34 |
| 4,430,074 | 2/1984 | Mooring ............................... 604/49 |
| 4,449,538 | 5/1984 | Corbitt et al. ........................ 604/65 |
| 4,451,255 | 5/1984 | Bujan et al. ......................... 604/157 |
| 4,460,358 | 7/1984 | Somerville et al. ................. 604/250 |
| 4,484,599 | 11/1984 | Hanover et al. ................. 137/636.1 |
| 4,512,764 | 4/1985 | Wunsch ................................ 604/80 |
| 4,533,347 | 8/1985 | Deckert . |
| 4,553,958 | 11/1985 | Lecocq ................................ 604/246 |
| 4,559,036 | 12/1985 | Wunsch .............................. 604/250 |
| 4,604,093 | 8/1986 | Brown et al. ......................... 604/81 |

FOREIGN PATENT DOCUMENTS

| | | | |
|---|---|---|---|
| 2849335 | 1/1980 | Fed. Rep. of Germany ...... 364/413 |
| 2855713 | 6/1980 | Fed. Rep. of Germany ........ 604/67 |
| 1130107 | 1/1957 | France ..................................... 251/9 |

Primary Examiner—John D. Yasko
Assistant Examiner—Mario Costantino
Attorney, Agent, or Firm—Kinney & Lange

[57] ABSTRACT

A multiple solution IV administration system includes a plurality of IV fluid sources which are connected by flexible tubing to the inlet of an IV pump. A sequence valve suspended from the tubing selectively pinches off all but one tube so that one source at a time is connected to the inlet. The sequence valve is controlled as a function of the accumulated volume pumped by the pump for each fluid and a stored volume limit for that fluid. When the accumulated volume of one IV fluid reaches its volume limit, the sequence valve is changed to connect a different source to the inlet of the IV pump. The desired volume limits and rates are entered manually and are checked automatically to protect against setup errors.

17 Claims, 3 Drawing Figures

MULTIPLE SOLUTION IV SYSTEM WITH SETUP ERROR PROTECTION

REFERENCE TO COPENDING APPLICATIONS

This application is a continuation-in-part of application Ser. No. 676,009, filed Nov. 29, 1984.

Reference is made to application Ser. No. 676,020, by G. K. Archibald and F. Slaker entitled "Sequence Valve for Piggyback IV Administration" filed on Nov. 29, 1984, Archibald et al U.S. Pat. No. 4,637,817, and application of G. K. Archibald and F. Slaker, Ser. No. 798,331, filed Nov. 15, 1985, entitled "Sequence Valve For Piggyback IV Administration with Tube Reversal Prevention". All of these applications and patent applications are assigned to the same assignee as the present application.

BACKGROUND OF THE INVENTION

1. Field of the Invention

The present invention relates to administration of intravenous (IV) fluid. In particular, the present invention is an IV administration system which supplies multiple IV solutions or medications at predetermined intervals to a patient.

2. Description of the Prior Art

It is quite common in IV therapy to give a patient a primary solution and one or more secondary solutions or medications. The secondary (or "piggyback") medication is usually given several times a day. An example is when a patient is on antibiotics. It is desirable to have an IV pump and a sequencing valve that administers the primary and secondary solutions sequentially.

In the past, there have been IV pump systems which allow two fluids to be administered. In these systems, the secondary medication is pumped until the secondary container goes empty, and then the pump switches to the primary fluid. An example of this type of system is shown in U.S. Pat. No. 4,451,255. This proves to be a substantial burden to hospital personnel, particularly where the secondary medication is required several times a day. With the prior art systems, the medical personnel must change secondary medication bags several times each day.

SUMMARY OF THE INVENTION

The present invention is an improved IV administration system which has a valve between the inlet of an IV control device (such as an IV pump or controller) and a plurality of sources of different IV fluids. The valve operates in response to a valve control signal to connect sequentially the sources to the inlet of the IV pump.

In the present invention, control means provides the valve control signal to the valve means after a predetermined volume of one of the IV fluids is pumped by the IV control device. By monitoring operation of the IV control device, the control means controls operation of the valve means to switch from one source to another when the predetermined volume of IV fluid from the one source has been pumped.

With the present invention, therefore, all of the medication for a day or more may be contained in one large bag, as opposed to smaller secondary bags that run dry after each delivery of secondary medication. Since the cost of large versus small bags is essentially the same, the system of the present invention achieves significant cost savings by reducing the number of bags which are used, and by reducing the number of times that the medical personnel must change bags.

While the ability to store and provide multiple doses of the piggyback or secondary solution within the secondary container is a significant advantage, the presence of multiple doses of secondary solution within the secondary container presents a potential for erroneous dosages. Typically, the secondary medication is intended to be provided to the patient only in limited doses. Although the secondary container may contain, for example, four or more doses, it is important that a patient does not receive multiple doses at one time due to malfunction or improper setup.

One potential cause of erroneous multiple doses of secondary solution is if the nurse enters erroneous setup control information (for example the wrong volume limit for the secondary solution). The present invention detects these errors automatically and provides an error signal if the setup control information does not meet a predetermined criterion.

DETAILED DESCRIPTION OF THE PREFERRED EMBODIMENTS

Figure 1:
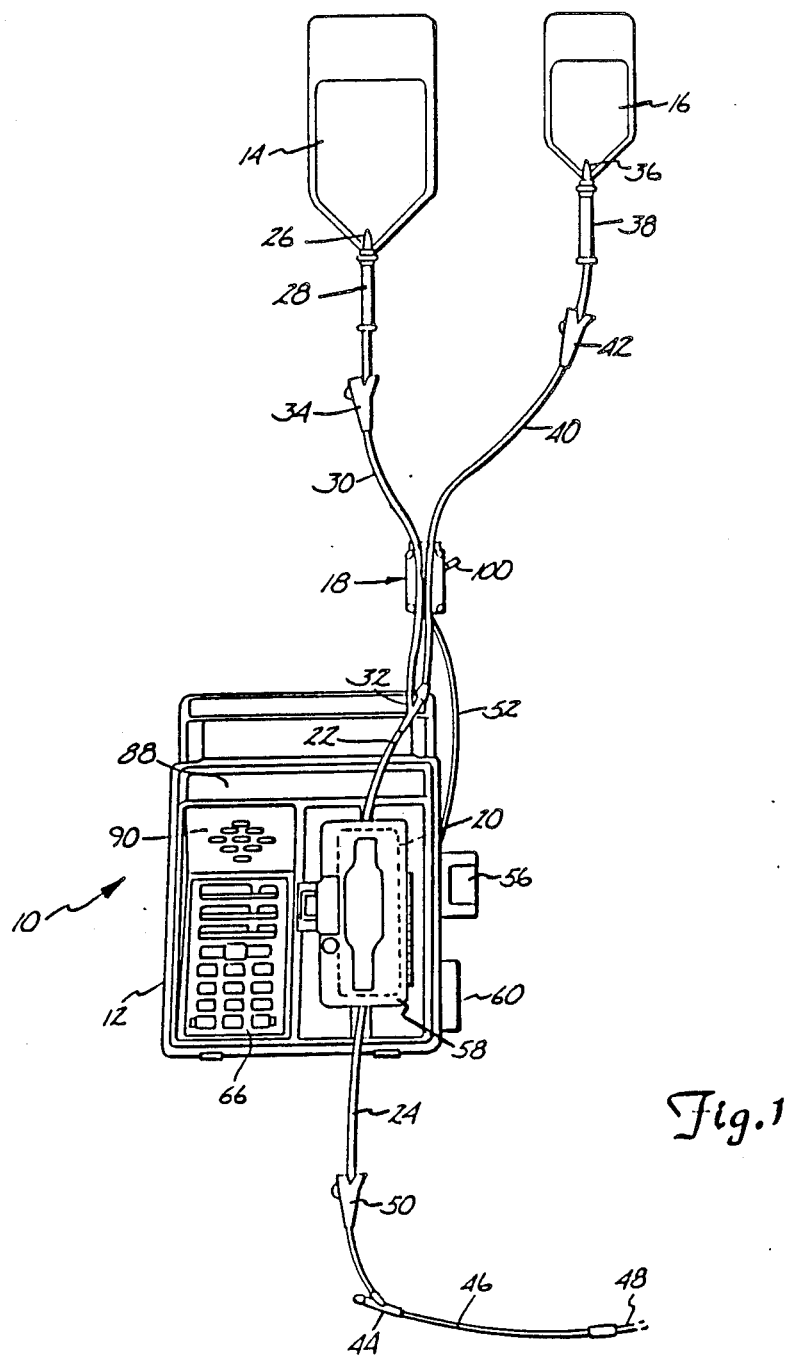
FIG. 1 is a partially schematic diagram of a preferred embodiment of the IV administration system of the present invention.

In the preferred embodiment shown in FIG. 1, IV administration system 10 includes IV pump 12, which pumps fluid from primary solution bag 14 or secondary (or piggyback) solution bag 16, to a patient (not shown). Sequence valve 18 is connected between bags 14 and 16 and pump 12 to select one of the bags 14 and 16 for connection to pump 12.

In the particular embodiment shown in FIG. 1, pump 12 is an IV pump such as the AVI GUARDIAN 400 pump manufactured by applicant's assignee AVI, inc. Pumps of this general type (which are described in U.S. Pat. No. 4,236,880) use a disposable multiple rolling diaphragm pumping chamber 20 which is inserted into pump 12. Pumping chamber 20 has an inlet tubing 22 connected at its inlet end, and an outlet tubing 24 at its outlet end. A drive mechanism within pump 12 causes relative movement of two of the rolling diaphragms of pumping chamber 20 and the operation of two valves to cause fluid to be pumped from inlet tubing 22 through pumping chamber 20 and out through outlet tubing 24 to the patient.

In the embodiment shown in FIG. 1, disposable multiple rolling diaphragm pumping chamber 20, inlet tubing 22 and outlet tubing 24 form a part of a disposable IV administration set which also includes primary spike 26, primary drip chamber 28, primary tubing 30, proximal Y connector 32, primary roller clamp 34, secondary spike 36, secondary drip chamber 38, secondary tubing 40, secondary roller clamp 42, distal Y connector 44, distal tubing 46, needle 48, and distal roller clamp 50.

Primary spike 26 is inserted into the lower end of primary bag 14, and is connected to the upper end of primary drip chamber 28. The lower end of primary drip chamber 28 is connected by primary tubing 30 to one leg of proximal Y connector 32.

Similarly, secondary spike 36 is inserted into the lower end of secondary bag 16 and is connected to the upper end of secondary drip chamber 38. The lower end of secondary drip chamber 38 is connected through secondary tubing 40 to the second leg of proximal Y connector 32. The third leg of Y connector 32 is connected to inlet tubing 22.

Primary tubing 30 and secondary tubing 40 pass through sequence valve 18, and at least one (preferably primary tubing 30) supports sequence valve 18. In the preferred embodiment of the present invention, sequence valve 18 is a light-weight, solenoid actuated device which initially pinches off primary tubing 30 to prevent flow from primary bag 14 while permitting flow from secondary bag 16 to pumping chamber 20. In response to a valve control signal received from pump 12 through multiconductor cable 52, sequence valve 18 switches so that secondary tubing 40 is pinched off and primary tubing 30 is unobstructed. When secondary tubing 40 is unobstructed and primary tubing 30 is pinched off, secondary (piggyback) bag 16 is connected to inlet tubing 22, and pump 12 pumps the secondary medication from piggyback bag 16 to the patient. Conversely, when secondary tubing 40 is pinched off and primary tubing 30 is unobstructed, the primary solution is pumped from primary bag 14 to the patient by IV pump 12.

The construction and operation of preferred embodiments of sequence valve 18 are described in detail in the copending applications referred to in "Reference to Copending Applications" above. That description is hereby incorporated by reference.

At the outlet end, outlet tubing 24 is connected through distal Y connector 44 to distal tubing 46. At the end of distal tubing 46 is needle 48, which is inserted into a vein of the patient. Distal Y connector 44 has another leg which is normally closed, but which allows the insertion of a syringe needle to introduce medication directly into distal tubing 46 as fluid is being pumped to the patient.

Roller clamps 34, 42 and 50 are used by medical personnel during the installation of the IV administration set into pump 12, during initial set-up, and during removal of the IV administration set.

Figure 2:
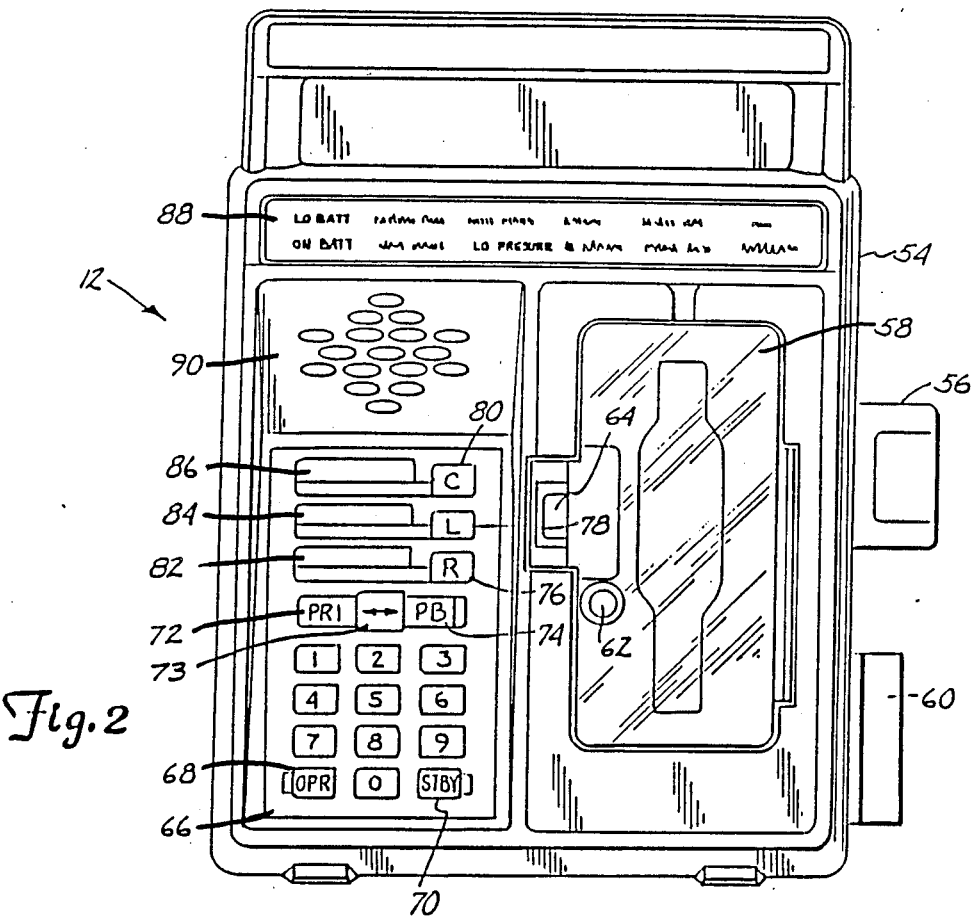
FIG. 2 is a front view of the IV pump of FIG. 1.

FIG. 2 shows a front view of pump 12. Pump 12 includes a housing 54 which contains the electrical control circuitry and the mechanical portions of the pump which interact with disposable pumping chamber 20. Pump 12 is supported on an IV stand or pole (not shown) by pole clamp 56. Door 58 covers a receptacle into which disposable pumping chamber 20 is inserted. In the embodiment shown in FIG. 2, the opening of door 58 requires operation of the three separate devices: load control handle 60, door lock 62, and door latch 64. During normal operation, when the IV administration set is installed with pumping chamber 20 within the receptacle of pump 12, door 58 is closed as shown in FIG. 2.

In the lower left corner of the front of pump 12 is control panel 66, which includes a keyboard formed by numerical key pads ("0" through "9"), operate key pad (OPR) 68, standby key pad (STBY) 70, PRIMARY indicator 72, PRIMARY-PIGGYBACK toggle key pad 73, PIGGYBACK indicator 74, RATE key pad 76, volume limit (LIMIT) key pad 78, and volume infused clear (CLEAR) key pad 80. Control panel 66 also includes three digital displays: rate display 82, volume limit display 84, and volume infused display 86.

Pump 12 also includes indicator panel 88, (which provides visual indication of different error or alarm conditions), and audio alarm annunciator 90.

Figure 3:
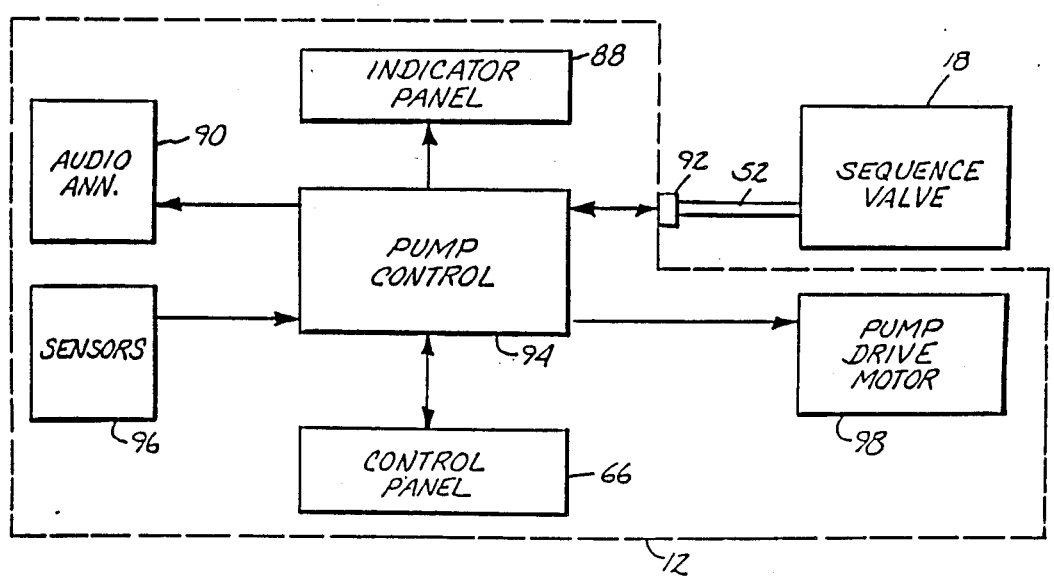
FIG. 3 is an electrical block diagram of the system of FIG. 1.

FIG. 3 is an electrical block diagram of pump 12 and sequence valve 18, which are connected together by multiconductor cable 52 and connector 92. Sequence valve 18 receives a valve control signal from pump 12, and provides a valve state signal, which indicates which fluid line (primary tubing 30 or secondary tubing 40) is occluded.

The operation of pump 12 is controlled by pump control 94, which in preferred embodiments includes a microcomputer, together with associated memory, timing and clock circuitry and appropriate interface circuitry. Pump control 94 receives input signals from control panel 66, from sensors 96 (which sense various operating conditions or parameters such as output pressure, air bubbles in the IV administration set, empty bags and opening of door 58), and from sequence valve 18. Pump control 94 provides outputs to displays 82, 84 and 86 of control panel 66, indicator panel 88, audio annunciator 90 and to pump drive motor 98. In addition, when sequence valve 18 is connected to pump 12 and a piggyback operation has been selected, pump control 94 provides the valve control signal to sequence valve 18.

Control panel 66 allows the medical personnel to "set up" an IV administration schedule so that predetermined volumes of the primary and secondary solutions are delivered at predetermined rates. Pump control 94 controls the operation of both sequence valve 18 and pump drive motor 98, so that it controls both the particular solution being pumped at any given time, and the rate at which the fluid is being pumped.

By depressing STBY key pad 70, the medical personnel places pump 12 in a standby mode. This allows changing or resetting of both rates and volume limits for both the primary and piggyback solutions. The primary solution rate is selected by depressing PRIMARY-PIGGYBACK toggle key pad 73 (toggling to the primary mode) and then RATE key pad 76, followed by the keys representing the numerical value desired. The primary volume limits can then be set by pressing LIMIT key pad 78 and then using the numerical keys to enter the desired numerical limit for the primary solution.

For the piggback or secondary solution, PRIMARY-PIGGYBACK toggle key pad 73 is pressed to toggle to the piggback mode. RATE key pad 76 is then pressed, followed by appropriate numerical keys to enter the piggyback rate. LIMIT key pad 78 is then depressed, followed by selected numerical key pads to set the piggback volume limit.

Pump control 94 stores the rates and volume limits entered for both the primary solution and the piggyback solution. These stored values are used, together with an accumulated volume infused value in controlling sequence valve 18 as well as pump drive motor 98.

In a preferred embodiment of the present invention, sequence valve 18 is a spring loaded, solenoid actuated device which initially occludes primary tubing 30 so that the secondary solution is pumped first. Sequence valve 18 is placed in this initial condition by inserting primary tubing 30 into one slot of sequence valve 18 and then cocking lever 100 so that primary tubing 30 is occulded. Secondary tubing 40 is then inserted into an adjacent slot alongside primary tubing 30 in sequence valve 18 as shown in FIG. 1.

Operation of pump 12 in the piggyback mode is initiated by depressing OPR key pad 68. Pump control 94 provides pump drive control signals to pump drive motor 98 which cause motor 98 to produce the pumping rate stored for the piggyback solution. As pump drive motor 98 is operated, pump control 94 maintains an accumulated value which represents the amount of secondary solution which has been pumped with sequence valve 18 in its initial setting. When that accumulated value reaches the piggyback volume limit stored by pump control 94, a valve control signal is produced which causes sequence valve 18 to change state. Sequence valve 18, in response to the valve control signal, occludes secondary tubing 40, and allows primary solution to flow through primary tubing 30, to inlet tubing 22. Upon receiving the signal from sequence valve 18 indicating that the change has been made, pump control 94 provides pump drive signals which cause pump drive motor 98 to operate at the pumping rate selected for the primary solution. Pump control 94 again maintains an accumulated value which represents the amount of primary solution which has been pumped. This value is displayed on volume infused display 86. When the accumulated value reaches the stored primary volume limit, pump control 94 halts operation of pump drive motor 98 and provides an indication through indicator panel 88 and audio annunciator 90 that both the piggyback and primary administration has been completed. At that point, the medical personnel responsible for the IV administration are required to intervene to set a new schedule of primary and piggyback rates and volume rates.

The system of the present invention is advantageous because all of the medication for a single day or for several days can be stored in one large secondary bag 16, as opposed to much smaller secondary bags which run dry after each administration of that medication. For example, if a patient is to receive 50 milliliters of secondary medication four times a day, four bags would be required with the prior art systems, in which the switching from the secondary bag to the primary solution is determined by when the secondary bag is empty. With the system of the present invention, one 200 milliliter bag can be used for the entire day. Since a large or a small bag costs essentially the same, there is a cost saving just by virtue of the reduced number of bags. In addition, the system significantly reduces the amount of time which is required of medical personnel. It is not necessary to change the secondary bag 16 after each administration of medication, and in fact the present invention allows the secondary medication to be provided multiple times without a change in the secondary bag.

By use of pump control 94 within housing 54 of pump 12 to control operation of both pump 12 and sequence valve 18, the size, weight, complexity and cost of sequence valve 18 are significantly reduced. As a result, sequence valve 18 can be suspended from the tubing (e.g. primary tubing 30) rather than requiring separate clamping to a pole. This makes sequence valve 18 simpler and easier to use, and makes it portable so that sequence valve 18 can be moved wherever pump 12 is moved.

As stated above, the ability to store and provide multiple doses of the piggyback or secondary solution within secondary container 16 is a significant advantage of the present invention. The presence of multiple doses of secondary solution within secondary container 16 also requires caution. Typically, the secondary medication is intended to be provided to the patient only in limited doses. Although secondary container 16 may contain four or even six doses, it is important that a patient will not receive multiple doses at one time due to malfunction or improper setup.

One potential cause of errorenous multiple doses of secondary solution is if the nurse enters the wrong volume limit through control panel 66. In preferred embodiments, the present invention provides simple yet effective means for identifying erroneous volume limits for the secondary solution which have been entered by a nurse.

It has been observed that the volume limit is usually a numerical value which is less than the numerical value of the pump rate. A simple first error check, therefore, is for pump control 94 to compare the volume limit for the secondary solution with the pump rate. If the volume limit is greater than the pump rate, pump control 94 provides an audible signal through annunciator 90 which indicates to the nurse that the setup is erroneous. Pump control 94 also will not permit the pump to start operation until the error has been corrected. Thus the nurse must make the appropriate change before starting operation of pump. In cases where the rate intentionally is not larger than the volume limit, an override is provided. The override procedure, which involves entering further inputs through control panel 66, is non-standard and therefore causes the the nurse to reevaluate the values being entered (and perhaps check their accuracy with the pharmacist or physician).

A second error check, which can be used alone or in conjunction with the first error check, is for the numerical value of the secondary solution volume limit to have a known mathematical relationship to the pump rate. For example, the pharmacist may be required to specify the secondary solution volume limit as an odd number and the pump rate as an even number (or vice versa). The known relationship between the secondary solution volume limit and the pump rate are used by pump control 94 to verify that the secondary solution volume limit and the pump rate have been correctly entered.

There are a variety of other relationships between the secondary solution volume limit and the pump rate (and/or the primary solution volume limit) which can be used. All that is required is that the relationship be known to the pharmacist who specifies the secondary solution volume limit and the other parameter(s) (e.g. pump rate or primary solution volume limit), and that known relationship be stored in memory within pump control 94, so that it can be used to perform an error check on the secondary solution volume limit when the pump is being set up.

Although the present invention has been described with reference to preferred embodiments, workers skilled in the art will recognize that changes may be made in form and detail without departing from the spirit and scope of the invention. For example, although the present invention has been described in the context of a system in which a primary and only one secondary bag are used, it is also applicable to more complex systems in which multiple secondary bags are used in conjunction with a primary bag.

Similarly, although the present invention has been described in the context of a specific type of IV pump and sequence valve sold by applicant's assignee, the present invention is applicable to other piggyback IV pump and controller systems as well.

What is claimed is:

1. An IV administration system comprising:
a first source of a primary IV fluid;
a second source of multiple doses of a secondary IV fluid;
an IV control device for delivering IV fluids at a rate determined by a rate control signal;
valve means for controlling fluid flow from the first and second sources to the IV control device as a function of a valve control signal;
means for connecting the IV control device to a patient;
control means for providing the rate control signal and the valve control signal to cause the IV control device to deliver the secondary IV fluid to the patient at a first rate until a first volume has been delivered and thereafter the primary IV fluid to the patient at a second rate until a second volume has been delivered;
means for providing input signals to the control means which select values for the first and second rates and the first and second volumes;
means for storing a mathematical relationship which interrelates the value of first volume with at least one other selected value; and
means responsive to the input signals for preventing operation of the IV control device unless the first volume and one of the other selected values satisfy the mathematical relationship.

2. An IV administration system comprising:
a first source of multiple doses of a first IV fluid;
a second source of a second IV fluid; an IV control device for delivering IV fluids at a a rate determined by a rate control signal;
valve means for controlling fluid flow from the first and second sources to the IV control device as a function of a valve control signal;
means for connecting the IV control device to a patient;
control means for providing the rate control signal and the valve control signal to cause the IV control device to deliver the first IV fluid to the patient at a first rate until a first volume has been delivered and the second IV fluid to the patient at a second rate until a second volume has been delivered;
user-actuated means for entering numerical values representing first and second rates and first and second volumes to be used by the control means; and
means for storing a required mathematical relationship between at least two of the numerical values;
error check means responsive to the user-actuated means for providing an error signal if at least two of the numerical values fail to satisfy the required mathematical relationship.

3. The IV administration system of claim 2 wherein the mathematical relationship is that the numerical value representing the first volume is less than another one of the numerical values.

4. The IV administration system of claim 2 wherein the mathematical relationship is that the numerical value representing one of the rates must be greater than the numerical value representing the first volume.

5. The IV administration system of claim 2 wherein the mathematical relationship is that one of the numerical values must be an odd number and one must be an even number.

6. The IV administration system of claim 2 and further comprising:
annunciator means responsive to the error signal for providing an audible signal 7. An IV administration system for administering a plurality of IV fluids to a patient, the system comprising:
a plurality of sources of IV fluid, each source providing a different IV fluid, and at least one of the sources having a volume capable of containing multiple doses of an IV fluid medication;
an IV control device having an inlet and an outlet for delivering IV fluid;
a plurality of flexible tubes connecting the plurality of sources to the inlet;
valve means between a plurality of sources and the inlet of the IV control device for selectively constricting all but one of the plurality of tubes to allow one of the sources to be connected to the inlet of the IV control device as a function of a valve control signal;
means for connecting the outlet of the IV control device to a patient;
control means for providing a valve control signal to the valve means as a function of volume delivered by the IV control device to cause the IV control device sequentially to deliver selected volumes of each of the IV fluids;
means for providing input signals to the control means which select the volumes; and
means for storing a mathematical criterion which interrelates values of the input signals including an input signal related to the selected volume of the IV fluid medication;
error check means responsive to the input signals for comparing the input signals to the stored mathematical criterion and providing an error signal if the input signals fail to meet the mathematical criterion.

8. The IV administration system of claim 7 wherein the input signals represent numerical values.

9. The IV administration system of claim 8 wherein the mathematical criterion is that an input signal representing a volume limit for the IV fluid medication is less than an input signal representing another operating parameter of the IV control device.

10. The IV administration system of claim 9 wherein the input signal representing another operating parameter represents a rate of flow produced by the IV control device.

11. An IV administration system comprising:
a first source of a primary IV fluid;
a second source of a secondary IV fluid, the second source having a volume sufficient to contain multiple doses of the secondary IV fluid;
means for sequentially delivering the secondary and primary IV fluids;
means for selecting parameters including a rate of delivery and volume limit for one dose of the secondary IV fluid to be delivered by the means for sequentially delivering;
means for storing mathematical relationship which the volume limit selected for one dose of the secondary IV fluid must have to another selected parameter if the volume limit has been properly selected; and
means for providing an error signal based upon the volume limit selected and the stored mathematical relationship if the volume limit selected for one dose of the secondary IV fluid does not satisfy the stored mathematical relationship.

12. The IV administration system of claim 11 wherein the selected parameter to which the volume limit selected for the secondary IV fluid must have the mathematical relationship is the rate of delivery.

13. The IV administration system of claim 12 wherein the stored mathematical relationship is that the volume limit for the secondary IV fluid is less than the rate of delivery.

14. The IV administration system of claim 12 wherein the stored mathematical relationship is that one of the rate of delivery and the volume limit is an even number and the other is an odd number.

15. The IV administration system of claim 11 wherein the means for sequentially delivering the secondary and primary IV fluids comprises:
 an IV control device for delivering IV fluids; and
 valve means for sequentially connecting the second source and the first source to the IV control device.

16. The IV administration system of claim 15 wherein the means for sequentially delivering further comprises:
 control means for controlling operation of the IV control device and the valve means as a function of the parameters selected.

17. The IV administration system of claim 11 wherein the selected parameter to which the volume limit selected for the secondary IV fluid must have the mathematical relationship is a volume limit for the primary IV fluid.

* * * * *